US010542894B2

(12) United States Patent
Zhao et al.

(10) Patent No.: US 10,542,894 B2
(45) Date of Patent: Jan. 28, 2020

(54) METHOD FOR MEASURING CARDIOVASCULAR AND RESPIRATORY PARAMETERS BASED ON MULTI-WAVELENGTH PHOTOPLETHYSMOGRAPHY

(71) Applicant: THE CHINESE UNIVERSITY OF HONG KONG, Hong Kong (CN)

(72) Inventors: Ni Zhao, Guangdong (CN); Yuanting Zhang, Hong Kong (CN); Jing Liu, Hubei (CN); Xiaorong Ding, Sichuan Province (CN); Wenxuan Dai, Zhejiang (CN); Yao Li, NingXia (CN); Shanshan Yuan, Guangdong Province (CN)

(73) Assignee: The Chinese University of Hong Kong, Hong Kong (CN)

( * ) Notice: Subject to any disclaimer, the term of this patent is extended or adjusted under 35 U.S.C. 154(b) by 396 days.

(21) Appl. No.: 15/388,486

(22) Filed: Dec. 22, 2016

(65) Prior Publication Data
US 2017/0172430 A1 Jun. 22, 2017

Related U.S. Application Data

(60) Provisional application No. 62/270,971, filed on Dec. 22, 2015.

(51) Int. Cl.
| A61B 5/026 | (2006.01) |
| A61B 5/1455 | (2006.01) |
| A61B 5/021 | (2006.01) |
| A61B 5/00 | (2006.01) |
| A61B 5/02 | (2006.01) |

(Continued)

(52) U.S. Cl.
CPC ........ *A61B 5/02108* (2013.01); *A61B 5/0064* (2013.01); *A61B 5/02028* (2013.01); *A61B 5/0245* (2013.01); *A61B 5/1102* (2013.01)

(58) Field of Classification Search
CPC .......... A61B 5/026; A61B 5/00; A61B 5/103; A61B 5/0205; A61B 5/1455
(Continued)

(56) References Cited

U.S. PATENT DOCUMENTS 5,991,654 A * 11/1999 Tumey ............... A61B 5/01
128/925
2009/0234245 A1 9/2009 Jaffe et al.
(Continued)

FOREIGN PATENT DOCUMENTS

| CN | 101002673 A | 7/2007 |
| CN | 101484065 A | 7/2009 |

(Continued)

OTHER PUBLICATIONS

International Search Report in International Application No. PCT/CN2016/111298, filed Dec. 21, 2016.
(Continued)

*Primary Examiner* — Carl H Layno
*Assistant Examiner* — Jon Eric C Morales
(74) *Attorney, Agent, or Firm* — Saliwanchik, Lloyd & Eisenschenk

(57) ABSTRACT

Accurate and effective methods for measuring cardiovascular and respiratory parameters are provided. The method for deriving a depth-specific photoplethysmography (PPG) signal from multi-wavelength PPG signals includes choosing light wavelength combinations, calibrating a multi-layer light-tissue interaction model referring to a physiological signal, and generating the depth-specific PPG signal from the multi-wavelength PPG signals based on the calibrated light-tissue interaction model. The disclosed method for cuff-less blood pressure measurement includes recording a physiological signal and multi-wavelength PPG signals of a predetermined body part, deriving the depth-specific PPG
(Continued)

signal reflecting the arterial blood volume with the physiological signal as a reference, calculating the pulse transit time (PTT) from the physiological signal and the derived arterial blood PPG signal, and calculating the blood pressure from the calibrated PTT and blood pressure relationship.

9 Claims, 6 Drawing Sheets

(51) Int. Cl.
  *A61B 5/0245* (2006.01)
  *A61B 5/11* (2006.01)
(58) Field of Classification Search
  USPC .................................................. 600/324, 479
  See application file for complete search history.

(56) References Cited

U.S. PATENT DOCUMENTS

2014/0073890 A1* 3/2014 Su .................. A61B 5/0215
                                                              600/324
2016/0367154 A1* 12/2016 Gladshtein ........... A61B 5/0261

FOREIGN PATENT DOCUMENTS

CN        101564290 B      5/2011
CN        103347439 A      10/2013

OTHER PUBLICATIONS

Asare, L. et al., Multi-spectral optoelectronic device for skin microcirculation analysis, Lithuanian Journal of Physics, 2012, pp. 59-62, vol. 52, No. 1, Lietuvos moksly akademija.

Rybynok, V. et al., Design and development of a novel multi-channel photoplethysmographic research system, 2013 IEEE Point-of-Care Healthcare Technologies (PHT), Jan. 16-18, 2013, pp. 267-270, IEEE, Bangalore, India.

Vahdani-Manaf, Nader et al., Biological assessments by innovative use of multi-wavelength photoplethysmographic signals time differences, Journal of Applied Sciences, 2015, pp. 1312-1317, vol. 15, Issue 11, www.ansinet.com, Asian Network for Scientific Information.

* cited by examiner

METHOD FOR MEASURING CARDIOVASCULAR AND RESPIRATORY PARAMETERS BASED ON MULTI-WAVELENGTH PHOTOPLETHYSMOGRAPHY

CROSS-REFERENCE TO RELATED APPLICATION

This application claims the benefit of U.S. Provisional Application Ser. No. 62/270,971, filed Dec. 22, 2015, the disclosure of which is hereby incorporated by reference in its entirety, including all figures, tables and drawings.

FIELD OF THE INVENTION

This invention relates to methods for measuring cardiovascular and respiratory parameters using a depth-specific photoplethysmography (PPG) signal derived from multi-wavelength PPG.

BACKGROUND

Photoplethysmography (PPG) is a simple and low-cost optical technique that can be used to detect blood volume changes in the microvascular bed of tissue and estimate cardiovascular and respiratory parameters. A PPG sensor system typically includes a light source and a light detector, and infrared (IR) light emitting diodes (LEDs) are usually used as the light emitting component. PPG is often used to make non-invasive measurements at the skin surface. The accuracy of extracting cardiovascular- and respiratory-related information from the PPG signals, however, is usually not satisfactory due the PPG signal being generated from a single-wavelength light that can only provide the overall blood volume changes along the light penetration path, but not the blood volume changes of a specific layer. For example, IR PPG measures the sum total of volume changes in any and all blood vessels (e.g., large and small arteries, arterioles, capillaries, venules, and veins) throughout the skin, while the blood pulsation signal of a specific layer like pure arterial blood volume changes cannot be separated out from the IR PPG signal. The inability to distinguish depth of single-wavelength PPG measurements intrinsically degrades the performance for estimating cardiovascular and respiratory parameters, which requires the physiological information of the blood vessels in certain depths.

Pulse Transit Time (PTT) is the time it takes the pulse pressure waveform to propagate through a length of the arterial tree, which is a promising method to measure blood pressure (BP) in a continuous and cuff-less manner. In PTT measurement, PPG is commonly used to mark the arrival of the pulse wave at a peripheral site. Because arteries and capillaries are different in blood vessel wall components and blood circulation paths, arterial blood volume waveform and capillary blood volume waveform have different morphologies, as well as a phase shift. In this sense, IR PPG or any other single-wavelength PPG signal is a superposition of various pulse wave functions of blood vessels in different types and depths, thus unable to reflect the pure arterial blood change in the deep layer of the skin. Therefore, PTT cannot be precisely measured with a single wavelength PPG in which the capillary blood pulsations fundamentally weaken PTT's BP tracking ability.

BRIEF SUMMARY OF THE INVENTION

Generating a depth-specific PPG signal that can reflect blood pulsation information within a specific tissue has great importance for measuring cardiovascular and respiratory parameters.

The instant invention provides accurate and effective methods for measuring cardiovascular and respiratory parameters, which can include deriving a depth-specific photoplethysmography (PPG) signal from multi-wavelength PPG signals. Deriving the depth-specific PPG signal can include choosing light wavelength combinations, calibrating a multi-layer light-tissue interaction model referring to a physiological signal like electrocardiography (ECG), and generating the depth-specific PPG signal from the multi-wavelength PPG signals based on the calibrated light-tissue interaction model. The generated depth-specific PPG signal can replace traditional single-wavelength PPG in various cardiovascular and respiratory applications with fundamentally improved performance. In addition, the instant invention also provides methods for measuring blood pressure using a depth-specific PPG signal, which is generated from infrared PPG (IR_PPG) and green PPG (G_PPG) to reflect the arterial blood volume pulsation.

BRIEF DESCRIPTION OF THE DRAWINGS

The present invention will hereafter be described with reference to the accompanying drawings, wherein like reference numerals denote like elements.

DETAILED DESCRIPTION OF THE INVENTION

Figure 1B:
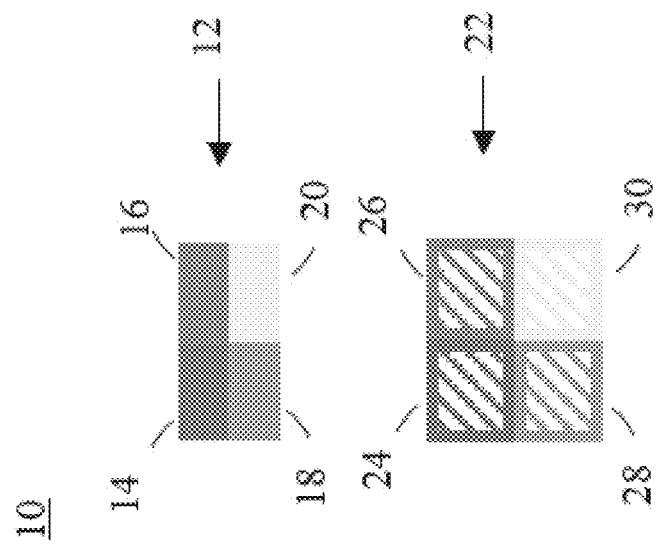
FIG. 1B shows a diagram of an element arrangement of a sensor with multiple LEDs and. multiple light detectors, according to an embodiment of the subject invention.

The instant invention provides accurate and effective methods for measuring cardiovascular and respiratory parameters by deriving depth-specific photoplethysmography (PPG) signals from multi-wavelength PPG signals, as well as methods of measuring blood pressure using depth-specific PPG signals that are generated from infrared PPG (IR_PPG) and green PPG (G_PPG) to reflect arterial blood volume pulsation.

In preferred embodiments, the methods of the instant invention provide accurate blood pressure measurements for clinical applications in bedside monitors and ambulatory health monitors. Advantageously, the methods of the instant invention provide more accurate measurements of PTT along the arteries as compared to conventional single-wavelength PPG methods.

The foregoing and other advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

In an embodiment, depth-specific PPG signal generation can include one or more of the following steps:
1. Determination of the range of target measuring depth or layer of the tissue based on the parameter to estimate;
2. Selection of wavelength combinations of PPG signals for deriving the depth-specific PPG signal; and/or
3. Extraction of the derived depth-specific PPG signals from the multi-wavelength PPG signals, wherein the depth-specific signals are proportional to the blood volume within a depth range beneath the measured site of the predetermined body part.

In many embodiments, the multi-wavelength PPG sensor can include a light source that emits light of two or more wavelengths, and a light detector. The light of different wavelengths penetrates the tissue to different depths depending on the absorption characteristics of the tissue layers, and different amounts of light of each wavelength come out of the tissue and are detected by the light detector. In some embodiments, the light source is one LED that can emit light in different wavelengths. In other embodiments, the light source is comprised of multiple small-sized LEDs that are packed closely, each LED emitting light at a different wavelength.

In some embodiments, the light detector comprises one photodetector with a wide wavelength response range whereby a multiplexer is used to separate the PPG signal of each wavelength. In other embodiments, the light detector comprises multiple detectors with high wavelength selectivity whereby multi-wavelength light can illuminate at the same time.

In preferred embodiments, the multi-wavelength PPG sensor emits multi-wavelength light to the peripheral vasculature in a predetermined body part and measures the intensity of the reflected light of each wavelength. The predetermined body part for measurement includes but is not limited to finger, thumb, hand, arm, abdomen, foot, or any body part directly associated with the peripheral vasculature.

Embodiments of the instant invention provide an algorithm for extracting the depth-specific PPG signals from multi-wavelength PPG signals. In some embodiments, multi-wavelength light is emitted from the light source, and light of different wavelengths penetrates the tissue to different depths. For example, PPG signals generated from the short penetrating light are considered to reflect the blood volume pulsation of the superficial layer of the tissue, while PPG signals generated from deep penetrating light are considered to reflect the blood volume pulsation at a deeper layer of the tissue. Advantageously, green or blue light is short penetrating light and red or infrared light is deep penetrating light.

In preferred embodiments, the methods of the instant invention measure the blood volume pulsation in the deep tissue layers only by removing the superficial blood pulsation from the deep penetration PPG signal. The methods are based on the Beer-Lambert's Law and provide that the depth-specific PPG is derived by dividing the deep-penetrating PPG signal amplitude by the short-penetrating PPG signal amplitude to the power of the absorption ratio (AR) of the two wavelengths.

In further embodiments, methods of the instant invention provide that the AR between different light wavelengths in the algorithm is determined within the value range that generates depth-specific PPG signals with a constant time offset to a preassigned reference physiological signal. In many embodiments, the reference physiological signal is an electrocardiography (ECG) signal. In other embodiments, the reference physiological signal is the same short wavelength PPG signal that is used to generate the depth-specific PPG signal. In yet other embodiments, the reference physiological signal is a ballistocardiography (BCG) signal or an impedance cardiography (ICG) signal.

In many embodiments, a method for cuff-less blood pressure (BP) measurement based on multi-wavelength PPG can include one or more of the following steps:
1. Recording an ECG signal and multi-wavelength PPG signals of a predetermined body part simultaneously;
2. Choosing the wavelength combination for deriving arterial blood PPG signals, wherein the wavelength combination includes short penetrating light that is considered to reflect the blood volume pulsation of the superficial layer of the tissue and deep penetrating light that is considered to reflect the blood volume pulsation at a deeper layer of the tissue;
3. Determining the light ARs for deriving an arterial blood PPG signal with the recorded ECG signal as a reference, wherein the AR selected from a value range that provides an inter beat interval (IBI) of the derived arterial blood PPG (D_PPG) that stably correlates with the IBI signal of the ECG is chosen;
4. Calculating the PTT using the ECG signal and arterial blood PPG signal derived from the multi-wavelength PPG; and
5. Calculating the BP by the calibrated BP-PTT model.

In preferred embodiments, the method for cuff-less BP measurement of the instant invention provides an arterial blood PPG signal for PTT calculation that improves PTT's tracking ability of BP.

In some embodiments, the arterial blood pressure is derived from two wavelengths PPG or three wavelengths PPG according to the accuracy requirement and computing ability of the system. Advantageously, the methods of the instant invention have no limitation in the BP estimation model from PTT. The relationship between PTT and BP can be linear, nonlinear, or adopt other complicated forms. In some embodiments, the ECG signal is replaced by other signals (including, but not limited to, short wavelength PPG, BCG signals and ICG signals) as the reference signal in determining AR values and calculating PTT.

In many embodiments, the methods of the instant invention are implemented in various physiological monitoring applications, such as smartwatches, fitness bands, and other wearable devices and bedside monitors. In some embodiments, a method can be implemented in wearable platforms, including but not limited to an Apple watch, LG Watch Urbane, and/or Motorola Moto 360 smart watch, by adding one light source to the wearable platform. Advantageously, the methods of the instant invention provide wider user acceptance compared to other wearable platforms due to improved accuracy based on the use of multi-wavelength PPG signals. Furthermore, the realization of the algorithm of the instant invention is more feasible to be implemented in smart wearable devices because it requires less computing power.

Multi-Wavelength PPG Sensor Probes.

Referring to FIG. 1, in one embodiment, a multi-wavelength PPG sensor probe 10 of the instant invention has a multi-wavelength light emitter 12 and a light detector 22. Preferably, the multi-wavelength light emitter 12 and the light detector 22 are small in size and/or flexible so as to improve the conformity to the skin and comfort for the user. Advantageously, as the sensor measures PPG signals in reflection mode, it can be placed on various body surfaces, such as a fingertip, wrist, thumb, hand, arm, abdomen, foot, earlobe, or any other body part directly associated with the peripheral vasculature.

In some embodiments, the multi-wavelength light emitter 12 of the instant invention includes multiple LEDs, for example, a blue LED 14, an infrared LED 16, a green LED 18, and a yellow LED 20 (FIG. 1). In preferred embodiments, the LEDs are closely packed, thus ensuring they illuminate the same tissue.

Figure 1A:
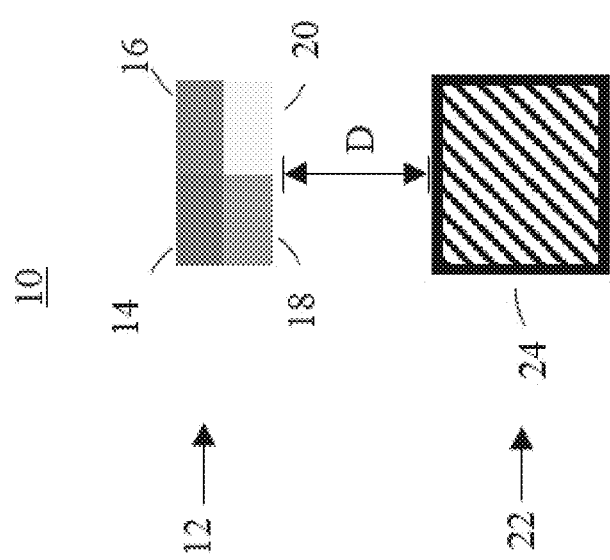
FIG. 1A shows a diagram of an element arrangement of a sensor with multiple LEDs and one light detector, according to an embodiment of the subject invention.

In some embodiments, the light detector 22 is a photodiode 24 with a wide spectral responsivity range (FIG. 1A). In one non-limiting example, a method of the instant invention provides sensors to acquire the multi-wavelength PPG signals, wherein the sensors' blue LED 14, infrared LED 16, green LED 18, and yellow LED 20 are turned on such that the mixed signals from the photodiode 24 that contains the reflected light information of different wavelengths are separated into four channels by a demultiplexer. In preferred embodiments, the distance D between the light emitter 12 and the light detector 22 is set appropriately to achieve good signal-to-noise ratio.

In other embodiments, the light detector 22 can include multiple light detectors with high selectivity to a certain band of light wavelength. In one non-limiting example, the light detector 22 includes a blue light sensitive light detector 24, a red light sensitive light detector 26, a green light sensitive light detector 28, and a yellow light sensitive light detector 30. Advantageously, light detectors 24, 26, 28, and 30 generate the PPG signals corresponding to the blue LED 14, red LED 16, green LED 18, and yellow LED 20, respectively, without a multiplexer. In preferred embodiments, the light detectors are packed closely to ensure that the PPG signals are measured from the same body part.

Multi-Wavelength Light Interaction with Tissue.

Figure 2:
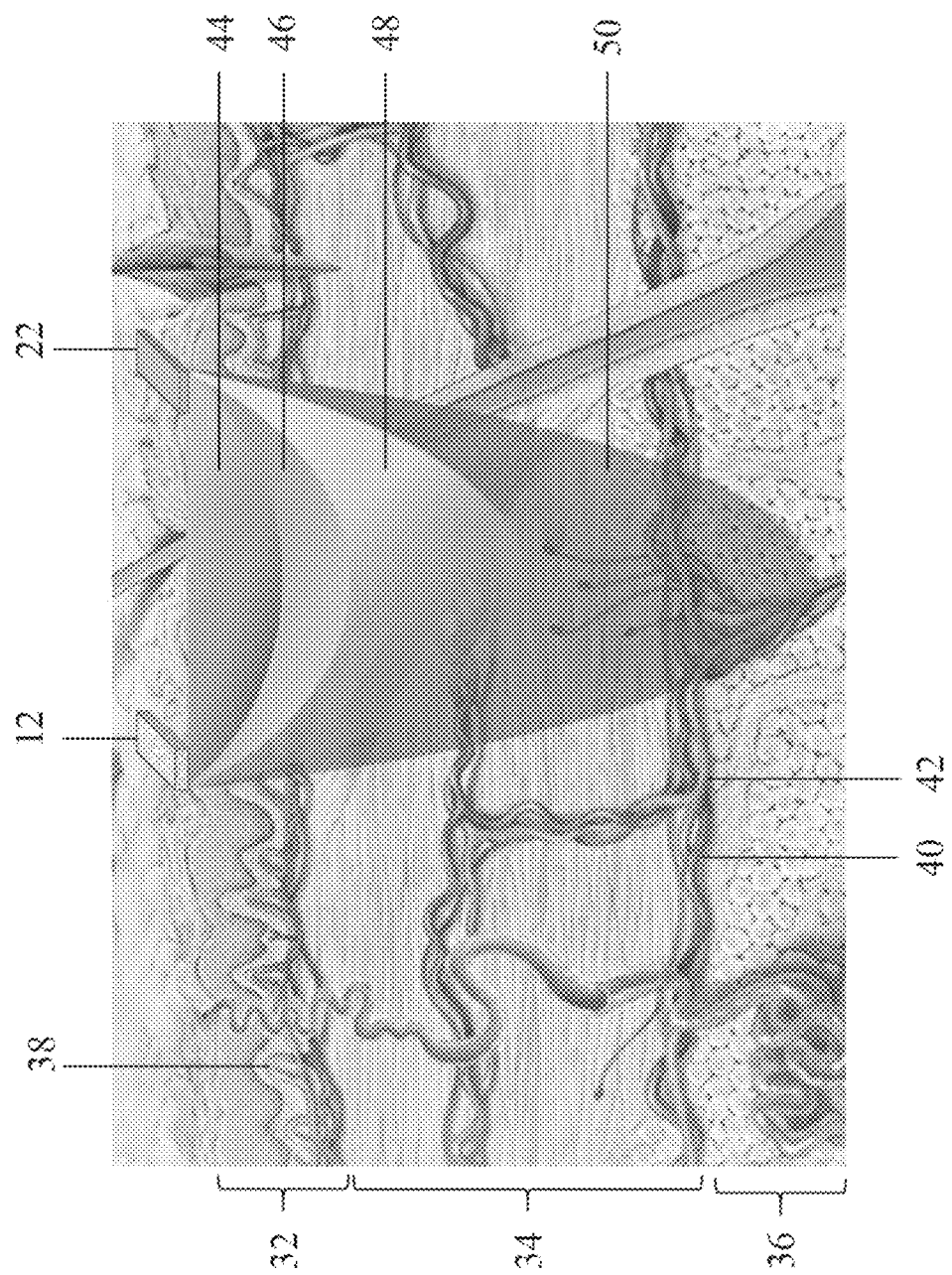
FIG. 2 shows the skin structure and the propagation of multi-wavelength light in the skin.

Referring to FIG. 2, skin has three layers: the epidermis 32, the outmost layer; the dermis 34, the layer under the epidermis 32 that is the connective tissue layer of skin; and the hypodermis 36, the layer underneath the dermis that merges with it and mainly contains adipose tissue. The arteries 40 supplying the skin are located deep in the hypodermis 36. Branches of the arteries 40, called arterioles 51, pass upwards to form a deep and a superficial plexus. Capillaries 38 are found beneath the epidermis 32, and are linked to the arterioles 51 and venules 52.

When light reaches the tissue, it is reflected, absorbed, scattered, and transmitted. As the light scattering and absorption coefficient of the tissue varies with the wavelength, the penetration ability of different light wavelengths is also different.

In a non-limiting example of a method of the instant invention, blue light 44, green light 46, yellow light 48, and infrared light 50 emitted from the light emitter 12 propagate within different tissue layers, and the light coming out of the tissue is detected by the light detector 22. As most of the blue light 44 and green light 46 are scattered by the epidermal layer 32, the penetration depth of blue light 44 may be only about 1.2 mm, while green light 46 penetrates a little deeper than blue light 44. The thickness of the epidermis can be about 0.8 mm to about 1.5 mm. Therefore, blue light 44 can only reach the capillaries, and green light 44 can penetrate through the epidermis 32 and reach some of the arterioles 51 in the dermis 34. Longer wavelength light like yellow light 48, can penetrate deep into the dermis and reach a large portion of the arterioles 51. In contrast, red light or infrared light 50 with strong penetration ability can go through the whole skin and reach the deep arteries 40 in the hypodermis 36.

Establishment of a Multi-Layer Models for Extraction of Pure Arterial Blood Volume.

Figure 3A:
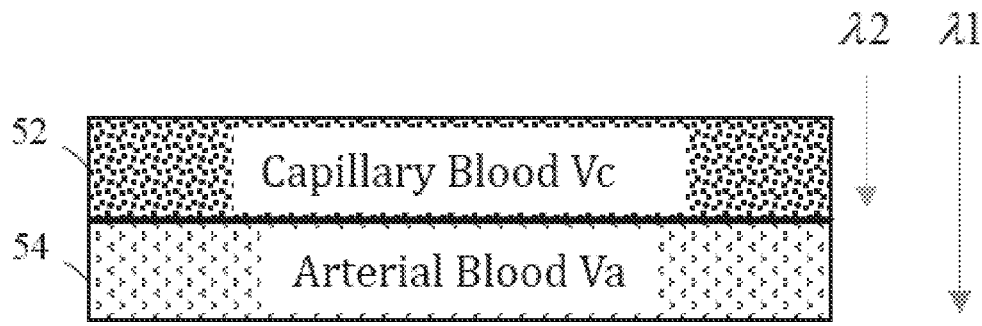
FIG. 3A shows a two-layer light-tissue interaction model.

Referring to FIG. 3A, in some embodiments, a method of the instant invention provides a two-layer model that extracts pure arterial blood volume, based on the physiological facts of the light-tissue interaction. In the two-layer model, the first layer 54 represents the epidermis as a homogenous layer highly perfused by capillary blood, and the second layer 53 represents the dermis 34 and hypodermis 36 (FIG. 2) as a homogenous layer highly perfused by arterial blood (FIG. 3A). In the two-layer model of the instant invention, light of wavelength λ2 penetrates the first layer 54 and reaches a portion of the second layer 53, while light of wavelength λ1 propagates through both layer 54 and layer 53. The following parameters in the model are provided:

$V_c$: Volume of capillary blood in the capillary blood layer 54

$V_a$: Volume of arterial blood in the arterial blood layer 53

$\varepsilon_{c1}$: Molar extinction coefficient of capillary blood in light wavelength λ1

$\varepsilon_{c2}$: Molar extinction coefficient of capillary blood in light wavelength λ2

$\varepsilon_{a1}$: Molar extinction coefficient of arterial blood in light wavelength λ1

$\varepsilon_{a2}$: Molar extinction coefficient of arterial blood in light wavelength λ2

$k_1$: The portion of arterial blood in layer 52 reached by light λ2

$I_{\lambda 1}$: Intensity of the incident light λ1

$I'_{\lambda 1}$: Intensity of light λ1 coming out from the surface $I_{\lambda 2}$: Intensity of the incident light λ2

$I'_{\lambda 2}$: Intensity of light λ2 coming out from the surface

The two-layer model, based on Beer-Lambert's that relates the attenuation of light to the properties of the material through which the light is traveling, can provide pure arterial blood volume information that is extracted by removing the capillary blood volume information registered by λ2 PPG from the λ1 PPG signal. The light intensity of light λ1 and λ2 coming out from the surface, namely the λ1 PPG amplitude and λ2 PPG amplitude, are described in Equation 1 and Equation 2.

$$I'_{\lambda 1} = I_{\lambda 1} e^{-\varepsilon_{c1} V_c} e^{-\varepsilon_{a1} V_a} \qquad \text{(Eq. 1)}$$

$$I'_{\lambda 2} = I_{\lambda 2} e^{-\varepsilon_{c2} V_c} e^{-\varepsilon_{a2} k_1 V_a} \qquad \text{(Eq. 2)}$$

The arterial blood volume can be expressed by Equation 3.

$$\frac{I'_{\lambda 1}}{(I'_{\lambda 2})^{\varepsilon_{c1}/\varepsilon_{c2}}} = \frac{I_{\lambda 1}}{(I_{\lambda 2})^{\varepsilon_{c1}/\varepsilon_{c2}}} e^{-(\varepsilon_{a1} - k_1 \varepsilon_{a2} \varepsilon_{c1}/\varepsilon_{c2}) V_a} \qquad \text{(Eq. 3)}$$

In Equation 3, as the terms $$\frac{I_{\lambda 1}}{(I_{\lambda 2})^{\varepsilon_{c1}/\varepsilon_{c2}}}$$

and $-(\varepsilon_{a1}-k_1\varepsilon_{a2}\varepsilon_{c1}/\varepsilon_{c2})$ can be treated as constants, the D_PPG signal with amplitude $$\frac{I_{\lambda 1}}{(I_{\lambda 2})^{\varepsilon_{c1}/\varepsilon_{c2}}}e^{-(\varepsilon_{a1}-k_1\varepsilon_{a2}\varepsilon_{c1}/\varepsilon_{c2})V_a}$$

can reflect the pure arterial blood information.

Figure 3B:
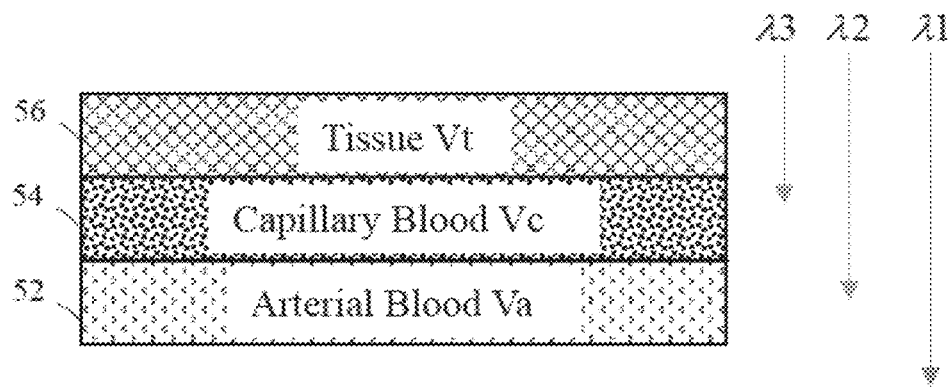
FIG. 3B shows a three-layer light-tissue interaction model.

Referring to FIG. 3B, in some embodiments, methods of the instant invention can provide a three-layer model for a more accurate estimation of the arterial blood volume. Compared to the two-layer model in FIG. 3A, the three-layer model provides an additional homogenous layer representing the superficial tissue 56. Light of wavelength λ3 can penetrate through the tissue layer 56 and a portion of the capillary blood layer 54. Other parameters additional to those included in the two-layer model are:

$V_t$: Volume of tissue in the first layer 56
$\varepsilon_{c3}$: Molar extinction coefficient of capillary blood in light wavelength λ3
$\varepsilon_{t1}$: Molar extinction coefficient of tissue in light wavelength λ1
$\varepsilon_{t2}$: Molar extinction coefficient of tissue in light wavelength λ2
$\varepsilon_{t3}$: Molar extinction coefficient of tissue in light wavelength λ3
$k_2$: The portion of capillary blood layer 54 reached by light λ2
$I_{\lambda 3}$: Intensity of the incident light λ3
$I'_{\lambda 3}$: Intensity of light λ3 coming out from the surface Similarly, λ1 PPG, λ2 PPG, and λ3 PPG signals measured at the skin surface can be expressed by Equation 4, Equation 5, and Equation 6, respectively.

$$I'_{\lambda 1}=I_{\lambda 1}e^{-\varepsilon_{t1}V_t}e^{-\varepsilon_{c1}V_c}e^{-\varepsilon_{a1}V_a} \quad (\text{Eq. 4})$$

$$I'_{\lambda 2}=I_{\lambda 2}e^{-\varepsilon_{t2}V_t}e^{-\varepsilon_{c2}V_c}e^{-\varepsilon_{a2}k_1V_a} \quad (\text{Eq. 5})$$

$$I'_{\lambda 3}=I_{\lambda 3}e^{-\varepsilon_{t3}V_t}e^{-\varepsilon_{c3}k_2V_c} \quad (\text{Eq. 6})$$

By eliminating the tissue volume information registered in λ3 PPG and the capillary blood volume information registered in λ2 PPG from the λ1 PPG that contains the volume information of all the layers, the arterial blood information can be calculated in Equation 7.

$$\frac{I'_{\lambda 1}}{(I'_{\lambda 3})^{\alpha_1-\alpha_2\alpha_3}(I'_{\lambda 2})^{\alpha_3}} = \frac{I_{\lambda 1}}{(I_{\lambda 3})^{\alpha_1-\alpha_2\alpha_3}(I_{\lambda 2})^{\alpha_3}}e^{-(\varepsilon_{a3}-\varepsilon_{a2}k_2\cdot\alpha_3)\cdot V_a} \quad (\text{Eq. 7})$$

where $$\alpha_1 = \frac{\varepsilon_{t1}}{\varepsilon_{t3}}, \alpha_2 = \frac{\varepsilon_{t2}}{\varepsilon_{t3}} \text{ and } \alpha_3 = \frac{\varepsilon_{c1}-\varepsilon_{c3}k_2\alpha_1}{\varepsilon_{c2}-\varepsilon_{c3}k_2\alpha_2}.$$

In Equation 7, as the term $$\frac{I_{\lambda 1}}{(I_{\lambda 3})^{\alpha_2-\alpha_1\alpha_3}(I_{\lambda 2})^{\alpha_3}}$$

and $-(\varepsilon_{a3}-\varepsilon_{a2}k_2\cdot a_3)$ can be treated as constants, the D_PPG signal with amplitude $$\frac{I_{\lambda 1}}{(I_{\lambda 3})^{\alpha_1-\alpha_2\alpha_3}(I_{\lambda 2})^{\alpha_3}}e^{-(\varepsilon_{a3}-\varepsilon_{a2}k_2\cdot\alpha_3)\cdot V_a}$$

can reflect the pure arterial blood information. Advantageously, three-layer models of the instant invention consider the influence of three tissue layers, including the superficial tissue, during light propagation, thus providing clearer arterial blood volume information compared to the two-layer models.

In preferred embodiments, the multi-layer models of the instant invention provide volume change information of a certain layer, namely a depth-specific PPG signal, derived from multi-wavelength PPG signals. In some embodiments, the multi-layer models of the instant invention provide volume change information of the capillary blood layer. The multi-layer models can provide volume change information of the arterial blood layer. Advantageously, the depth-specific PPG signals fundamentally improve the performance of PPG-based physiological monitoring applications.

Figure 4:
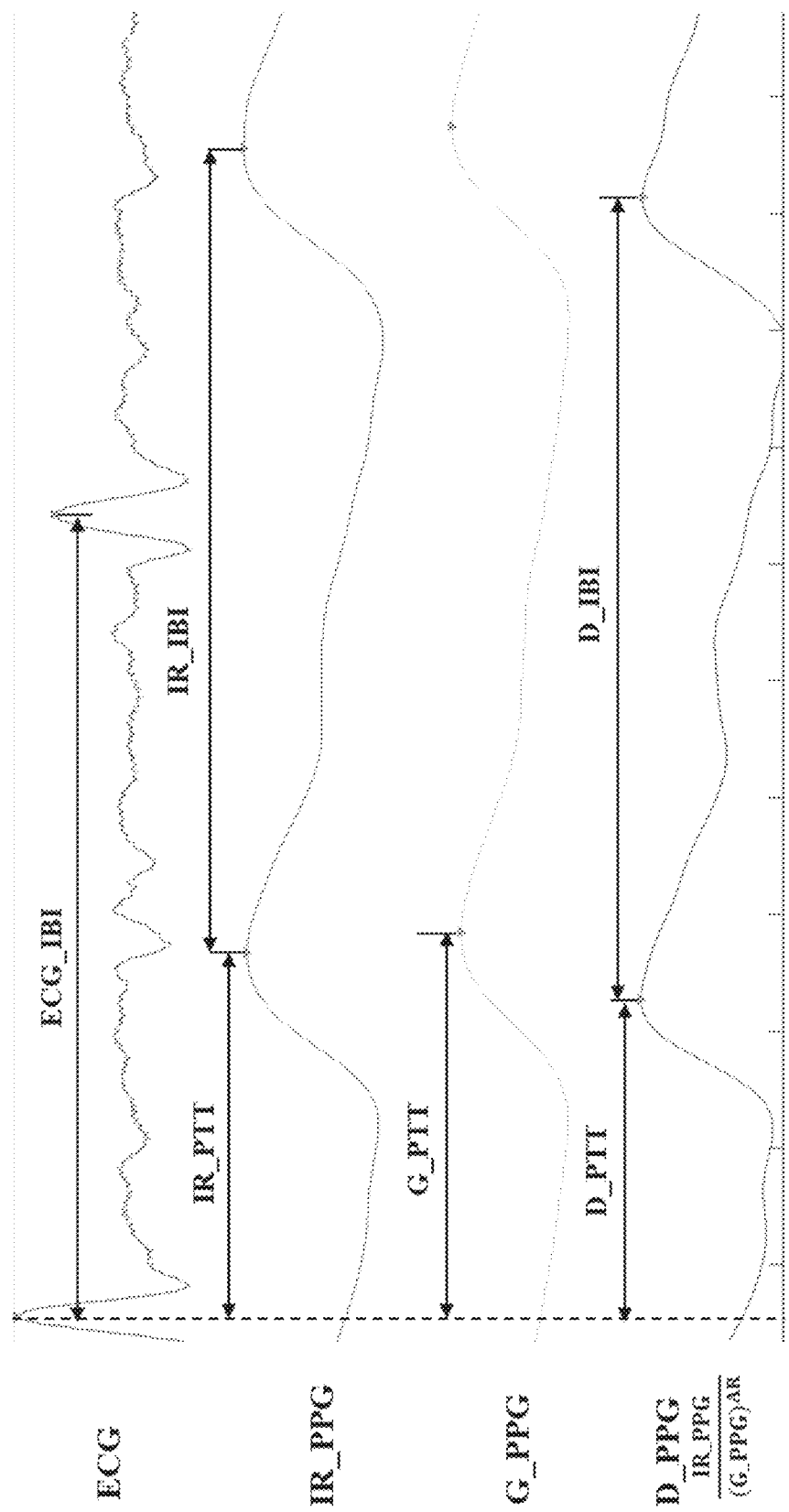
FIG. 4 shows feature extraction for a two-layer model based on ECG, infrared (IR) PPG and Green (G) PPG signals, according to an embodiment of the subject invention.

In one non-limiting example, methods of the instant invention provide the D_PPG from IR_PPG and G_PPG, where D_PPG reflects the arterial blood pulsation. Advantageously, the D_PPG shows an improved correlation between PTT and BP. Referring to FIG. 4, in many embodiments, the operation of deriving D_PPG from ECG, IR_PPG and G_PPG is based on the two-layer model. In preferred embodiments, the D_PPG is derived as the ratio of the IR_PPG amplitude and the G_PPG amplitude to a power of the AR, that is $$\frac{IR\_PPG}{(G\_PPG)^{AR}}.$$

In a further preferred embodiment, the ECG signal is used as a reference to decide the optimal value range of AR. Advantageously, because the periodical pulsations of the ECG and PPG signals are all generated by the beating heart, the IBI of the D_PPG signal matches the IBI of the ECG to a certain extent if the D_PPG only contains the arterial blood pulsation. As D_PPG can reflect pure arterial blood pulsation with a range of AR values, the synchrony level between IBI of the ECG and MI of the D_PPG derived with these AR values will become nearly unchanged. The ECG_IBI is defined as the time interval between the R peaks of the ECG, while the IR_IBI, G_IBI and D_IBI are defined as peak intervals of the respective waveforms (FIG. 4). The PTT is defined as the time interval between the R peak of the ECG waveform and the peak of the PPG waveform during the same heart cycle. Hence, IP_PTT, G_PTT, and D_PTT denote the PTT calculated from IR_PPG, G_PPG, and D_PPG respectively.

Figure 5:
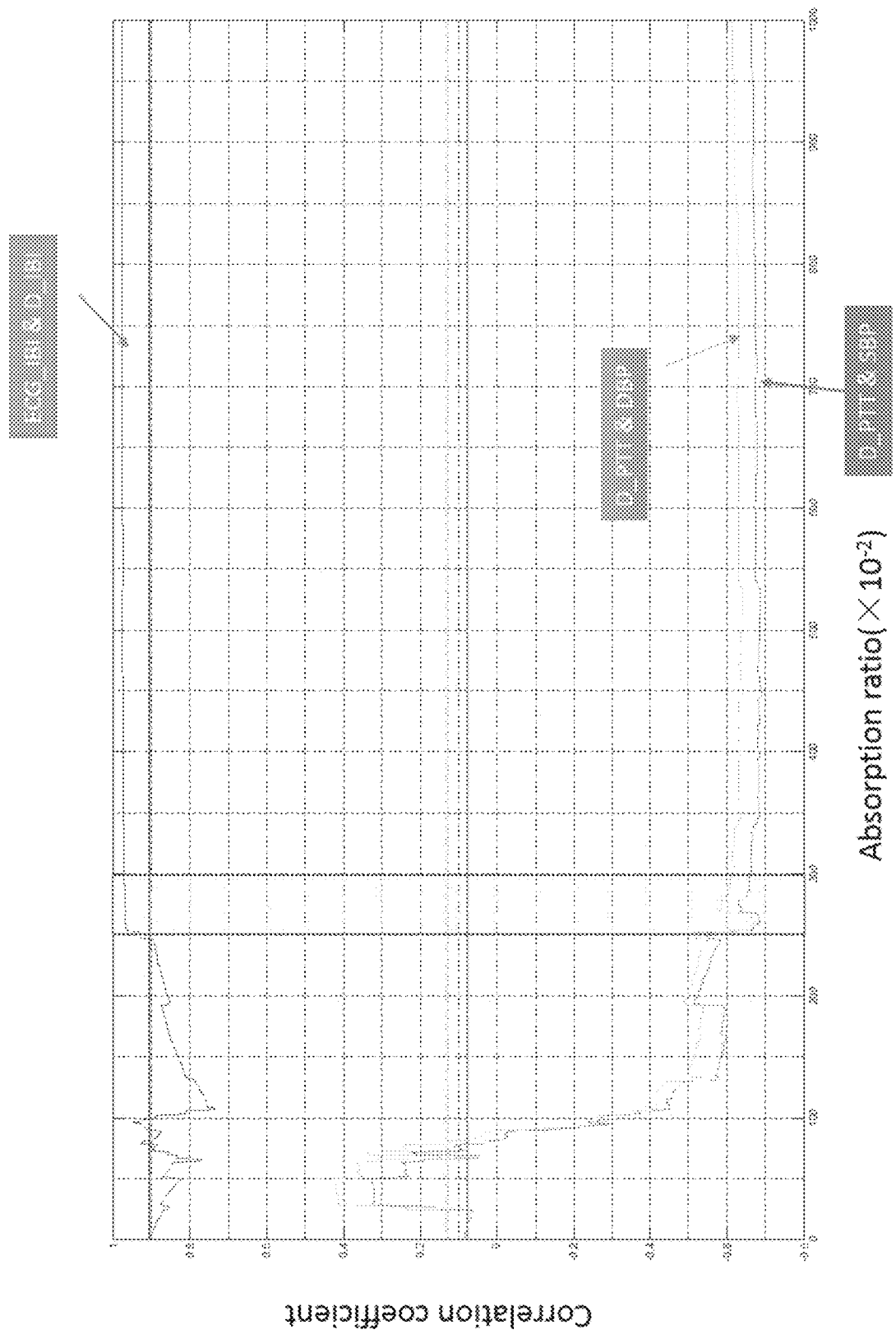
FIG. 5 shows an example result of blood pressure (BP) and Heart Rate (HR) tacking performance of a two-layer model with varying absorption ratio.

Referring to FIG. 5, in many embodiments, the correlation coefficients between ECG_IBI and D_IBI can be used to determine a AR value range for deriving a D_PPG signal. The absolute correlation coefficients between D_PTT and DBP (diastolic blood pressure); and D_PTT and SBP (systolic blood pressure) with varying ARs are also shown in FIG. 5. When AR equals zero, the D_PPG equals IR_PPG. In further embodiments, the correlation coefficient between ECG_IBI and D_IBI remains nearly unchanged in a certain range of AR value, at the same time, the correlation coefficient between D_PTT and DBP; and D_PTT and SBP will also stay stable in this AR value range. For example, the correlation relationship between ECG_IBI and D_IBI stays stable when AR is larger than 2.8. Meanwhile, strong and improved correlation coefficients are observed between D_PTT and DBP; and D_PTT and SBP, respectively, compared to those between IR_PTT and SBP; and IR_PTT and DBP (FIG. 5).

In further preferred embodiments, the methods of the instant invention use the ECG as reference to indicate the optimal AR value range for D_PPG. In other embodiments, the ECG signals are replaced by other physiological signals, including, but not limited to, short wavelength PPG, BCG and ICG.

Figure 6:
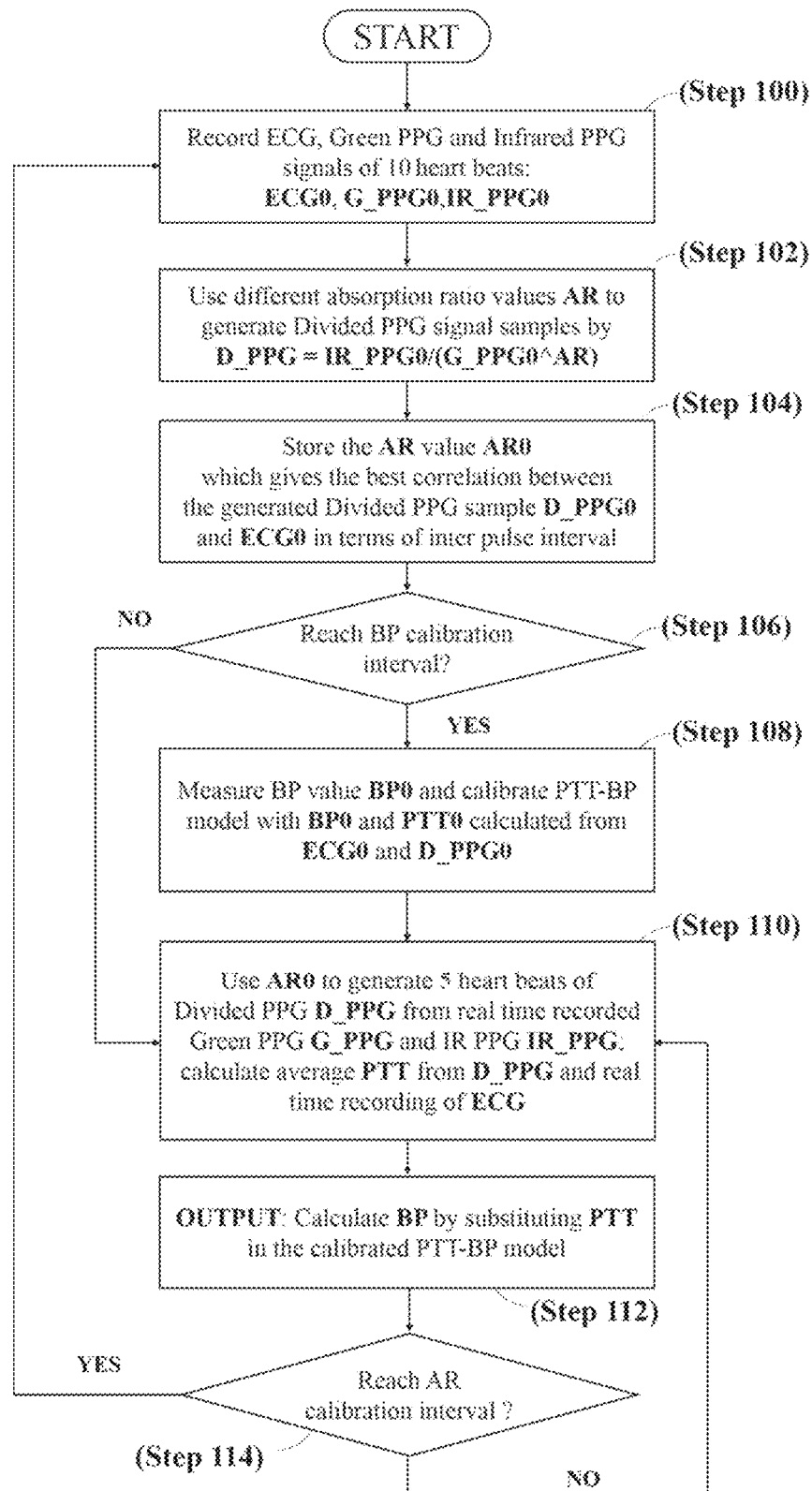
FIG. 6 shows a flowchart of an operation of measuring BP based on ECG and multi-wavelength PPG, according to an embodiment of the subject invention.

In a preferred non-limiting example, the BP can be monitored with ECG and multi-wavelength PPG sensors following the operation described in the work flow in FIG. 6. ECG, G_PPG and IR_PPG signals can be recorded for multiple heart beats (e.g., 10 heart beats) as ECG0, G_PPG0, and IR_PPG0 (Step 100). The recording period in Step 100 can be adjusted according to the specific application. Various D_PPG samples can be generated from IR_PPG0 and G_PPG0 using the relation IR_PPG0/(G_PPG0^AR) with different AR values (Step 102). The correlation coefficients between D_IBI of the D_PPG samples and ECG_IBI of ECG0 can be calculated, and the AR value that generates the D_PPG sample D_PPG0 best correlated with ECG0 in terms of IBI, can be stored as AR0 for deriving workable D_PPG signals in later steps (Step 104). It can be determined whether the D_PPG values obtained using the procedure of the previous steps gives D_PTT values that fall within an interval that is suitable for BP calibration (Step 106), wherein the calibration time interval and/or changes in physiological parameters, such as the heart rate exceeding a predetermined threshold, are considered. That is, the judgement condition can be whether the calibration time interval is reached, or whether changes in physiological parameters like heart rate exceed the predetermined thresholds.

In some embodiments, in which the BP calibration conditions are met, absolute BP values BP0 can be measured with the aid of certain BP measurement devices, and BP0 together with D_PTT0, which is the average D_PTT value calculated from ECG0 and D_PPG0, can be used to generate a calibrated PTT-BP model (Step 108).

In other embodiments, in which BP calibration conditions are not met in Step 106, ECG, IR_PPG, and G_PPG signals can be recorded (e.g., for every 5 heart beats) as ECG-n. IR_PPGn and G_PPGn (Step 110). The recording period can be adjusted according to the specific application. D_PPGn signals can be generated from IR_PPGn and G_PPGn with AR0, and the average D_PTTn can be calculated from D_PPGn and ECGn.

The BP can be estimated as BPn from D_PTTn by substituting D_PTTn in the calibrated PTT-BP model. It can be determined whether the calibration interval for AR is reached, wherein the judgment criteria can be a time interval or the threshold for changes of the parameter such as the estimated BP value BPn. In certain embodiments, if the AR calibration condition is not met, Step 110 will be executed to measure BP with the stored AR value AR0 again. In other embodiments, if the AR calibration condition is met, the series of processing steps starting with Step 100 will be repeated to fine-tune the process.

In certain embodiments, the process of measuring blood pressure of the instant invention (see FIG. 6) can be modified to adopt different models, different light wavelength combinations, and/or different cardiac signals (e.g., signals other than ECG). In some embodiments, the workflow and/or measuring principles can also be modified to measure other cardiovascular and respiratory parameters with multi-wavelength PPG.

"Cardiorespiratory parameters" include, but are not limited to, respiration rate, blood pressure, and cardiac rhythm.

"Cardiac disease states" include, but are not limited to, heart failure, arrhythmia, coronary artery disease, cardiomyopathy and endocarditis.

The methods and processes described herein can be embodied as code and/or data. The software code and data described herein can be stored on one or more computer-readable media, which may include any device or medium that can store code and/or data for use by a computer system. When a computer system reads and executes the code and/or data stored on a computer-readable medium, the computer system performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that is capable of storing computer-readable information/data. Computer-readable media should not be construed or interpreted to include any propagating signals. A computer-readable medium of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section, if present) are incorporated by reference in their entirety, including all figures and tables, to the extent they are not inconsistent with the explicit teachings of this specification.

What is claimed is:

1. A method for deriving a blood volume pulsation signal within a certain depth of a predetermined body part, the method comprising:
   determining a range of target measuring depth or layer of tissue in the predetermined body part;
   selecting wavelength combinations of photoplethysmography (PPG) signals to derive a PPG signal specific for the range of target depth or layer of tissue;
   emitting light of two or more different wavelengths to the predetermined body part and measuring multi-wavelength PPG signals; and extracting the derived depth-specific PPG signal from the multi-wavelength PPG signals, wherein the derived depth-specific PPG signal is proportional to the blood volume within the range of target depth or layer of tissue in the predetermined body part, wherein deriving the depth-specific PPG signal includes removing blood volume pulsation profiles in a superficial layer detected by a shallow penetrating light from the blood volume pulsation profiles in a deep layer detected by a deep penetrating light, and wherein removing blood volume pulsation profiles detected by the shallow penetrating light comprises:
building a multiple-tissue layer model based on the measured multi-wavelength PPG signals and the derived depth-specific PPG signal by incorporating parameters comprising light wavelengths, light absorption coefficients, and light penetration depths;
determining the light absorption ratios of different light wavelengths; and
deriving the depth-specific PPG signal that reflects the blood volume pulsation in a specific tissue depth from multi-wavelength PPG signals by substituting the light absorption ratios that reflect the difference of the tissue absorption characteristics of the different light wavelengths.

2. The method according to claim 1, wherein determining the light absorption ratios comprises selecting the absorption ratio value range that gives the constant correlation of inter beat intervals between the derived depth-specific PPG signal and selected cardiac signals.

3. The method according to claim 1, wherein the multiple-tissue layer model is a two-tissue layer model and the derived depth-specific PPG signal with amplitude $$\frac{I_{\lambda 1}}{(I_{\lambda 2})^{\varepsilon_{c1}/\varepsilon_{c2}}} e^{-(\varepsilon_{a1} - k_1 \varepsilon_{a2} \varepsilon_{c1}/\varepsilon_{c2}) V_a}$$

is obtained,
where $I'_{\lambda 1}$ is the intensity of light of a first wavelength coming out from the surface; $I'_{\lambda 2}$ is the intensity of light of a second wavelength different from the first wavelength coming out from the surface; $V_a$ is the volume of arterial blood in an arterial blood layer of the predetermined body part; $\varepsilon_{c1}$ is the molar extinction coefficient of capillary blood in the light of the first wavelength; and $\varepsilon_{c2}$ is the molar extinction coefficient of capillary blood in the light of the second wavelength.

4. The method according to claim 1, wherein the multiple-tissue layer model is a three-tissue layer model and the derived PPG signal with amplitude $$\frac{I_{\lambda 1}}{(I_{\lambda 3})^{\alpha_1 - \alpha_2 \alpha_3}(I_{\lambda 2})^{\alpha_3}} e^{-(\varepsilon_{a3} - \varepsilon_{a2} k_2 \cdot \alpha_3) V_a}$$

is obtained,
where $I'_{\lambda 1}$ is the intensity of light of a first wavelength coming out from the surface; $I'_{\lambda 2}$ is the intensity of light of a second wavelength different from the first wavelength coming out from the surface; $I'_{\lambda 3}$ is the intensity of light of a third wavelength different from both the first and second wavelengths coming out from the surface; $V_a$ is the volume of arterial blood in an arterial blood layer of the predetermined body part, where $$\alpha_1 = \frac{\varepsilon_{t1}}{\varepsilon_{t3}},\ \alpha_2 = \frac{\varepsilon_{t2}}{\varepsilon_{t3}}\ \text{and}\ \alpha_3 = \frac{\varepsilon_{c1} - \varepsilon_{c3} k_2 \alpha_1}{\varepsilon_{c2} - \varepsilon_{c3} k_2 \alpha_2};$$

$\varepsilon_{t1}$ is the molar extinction coefficient of tissue in the light of the first wavelength; $\varepsilon_{t2}$ is the molar extinction coefficient of tissue in the light of the second wavelength; $\varepsilon_{t3}$ is the molar extinction coefficient of tissue in the light of the third wavelength; $\varepsilon_{c3}$ is the molar extinction coefficient of capillary blood in the light of the third wavelength; and $k_2$ is the portion of capillary blood layer reached by the light of the second wavelength.

5. The method according to claim 1, further comprising using the depth-specific PPG signal to estimate at least one cardiorespiratory parameter selected from respiration rate, blood pressure, cardiac rhythm, and different cardiac disease states including heart failure, arrhythmia, coronary artery disease, cardiomyopathy, and endocarditis.

6. A method for cuff-less blood pressure measurement, the method comprising:
emitting light of two or more different wavelengths to a predetermined body part and recording multi-wavelength photoplethysmography (PPG) signals;
developing a model for a relationship between the recorded multi-wavelength PPG signals and desired depth-specific PPG signals representing: (1) pure arterial blood volume changes in a reticular dermis and in a hypodermis of the predetermined body part; and (2) pure capillary blood changes in a papillary dermis of the predetermined body part;
selecting a wavelength combination for deriving the desired depth-specific PPG signals;
deriving the desired depth-specific PPG signals based on the developed model for the relationship between the recorded multi-wavelength PPG signals and the desired depth-specific PPG signals;
extracting features in time domain, amplitude domain, and frequency domain from the derived depth-specific PPG signals;
developing an algorithm for estimating blood pressure from the extracted features; and
calibrating the developed algorithm and using the algorithm to estimate blood pressure from the extracted features.

7. The method according to claim 6, further comprising recording a physiological signal of the predetermined body part,
wherein extracting the features in time-domain, amplitude domain, and frequency domain comprises extracting the features from the physiological signal and the derived depth-specific PPG signals.

8. The method according to claim 7, wherein the physiological signal is an electrocardiogram (ECG) signal.

9. The method according to claim 7, wherein the physiological signal is a ballistocardiography (BCG) signal, an impedance cardiography (ICG) signal, or a short wavelength PPG signal.

* * * * *